(12) United States Patent
Yamauchi et al.

(10) Patent No.: US 11,718,599 B2
(45) Date of Patent: *Aug. 8, 2023

(54) METHOD FOR PRODUCING CYCLIC CARBONATE HAVING UNSATURATED GROUP, AND NOVEL CYCLIC CARBONATE

(71) Applicant: DAIKIN INDUSTRIES, LTD., Osaka (JP)

(72) Inventors: Akiyoshi Yamauchi, Osaka (JP); Kotaro Hayashi, Osaka (JP); Yuuki Suzuki, Osaka (JP); Yoshihiro Yamamoto, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 98 days.

This patent is subject to a terminal disclaimer.

(21) Appl. No.: 16/754,980

(22) PCT Filed: Sep. 20, 2018

(86) PCT No.: PCT/JP2018/034868
§ 371 (c)(1),
(2) Date: Apr. 9, 2020

(87) PCT Pub. No.: WO2019/073775
PCT Pub. Date: Apr. 18, 2019

(65) Prior Publication Data
US 2021/0198228 A1    Jul. 1, 2021

(30) Foreign Application Priority Data

Oct. 11, 2017   (JP) ................... 2017-197971
Mar. 7, 2018    (JP) ................... 2018-040689

(51) Int. Cl.
*C07D 317/40*    (2006.01)
*C07D 317/36*    (2006.01)

(52) U.S. Cl.
CPC ........ *C07D 317/40* (2013.01); *C07D 317/36* (2013.01)

(58) Field of Classification Search
CPC ............... C07D 317/40; C07D 317/36
See application file for complete search history.

(56) References Cited

U.S. PATENT DOCUMENTS

| | | | |
|---|---|---|---|
| 4,859,229 A | 8/1989 | Wenger et al. | |
| 2002/0019378 A1 | 2/2002 | Angell et al. | |
| 2005/0214649 A1 | 9/2005 | Yew et al. | |
| 2011/0195991 A1 | 8/2011 | Mederski | |
| 2018/0118760 A1 | 5/2018 | Kawai et al. | |
| 2020/0280096 A1* | 9/2020 | Nakamura | C07C 69/003 |

FOREIGN PATENT DOCUMENTS

| | | |
|---|---|---|
| JP | 63-41466 A | 2/1988 |
| JP | 3-177410 A | 8/1991 |
| JP | 2000-513380 A | 10/2000 |
| JP | 2005-285765 A | 10/2005 |
| JP | 2009-541376 A | 11/2009 |
| JP | 5971830 B1 | 8/2016 |
| JP | 2017-147130 A | 8/2017 |
| WO | 2017/017210 A1 | 2/2017 |

OTHER PUBLICATIONS

RN865529-55-1, registry database compound, 2005.*
International Preliminary Report on Patentability with English Translation of Written Opinion of the International Searching Authority for PCT/JP2018/034868 dated Apr. 14, 2020.
Biggadike et al., "Selective Plasma Hydrolysis of Glucocorticoid γ-Lactones and Cyclic Carbonates by the Enzyme Paraoxonase: An Ideal Plasma Inactivation Mechanism", Journal of Medicinal Chemistry, 2000, vol. 43, No. 1, pp. 19-21 (3 pages total).

(Continued)

*Primary Examiner* — Sun Jae Yoo
(74) *Attorney, Agent, or Firm* — Sughrue Mion, PLLC

(57) ABSTRACT

A method for producing a cyclic carbonate represented by the following formula (1):

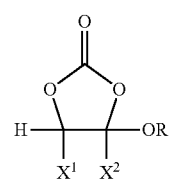

(1)

wherein $X^1$ and $X^2$ are the same as or different from each other, and are each a hydrogen atom, a fluorine atom, or a monovalent organic group; and R is an organic group containing one or more carbon-carbon unsaturated bonds. The method includes reacting an unsaturated cyclic carbonate represented by the following formula (A):

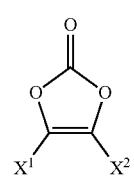

(A)

wherein $X^1$ and $X^2$ are defined as described above, and an alcohol represented by the formula (B): R—OH, wherein R is defined as described above, or an alkoxide thereof in the presence of a base, or reacting the unsaturated cyclic carbonate and the alkoxide. Also disclosed is a method for producing a cyclic carbonate.

11 Claims, No Drawings

(56) References Cited

OTHER PUBLICATIONS

Communication dated Dec. 22, 2020, from the European Patent Office in European Application No. 18865866.0.
International Search Report for PCT/JP2018/034868 dated Dec. 4, 2018 (PCT/ISA/210).

* cited by examiner

METHOD FOR PRODUCING CYCLIC CARBONATE HAVING UNSATURATED GROUP, AND NOVEL CYCLIC CARBONATE

CROSS REFERENCE TO RELATED APPLICATIONS

This application is a National Stage of International Application No. PCT/JP2018/034868 filed Sep. 20, 2018, claiming priority based on Japanese Patent Application No. 2017-197971, filed Oct. 11, 2017 and Japanese Patent Application No. 2018-040689 filed Mar. 7, 2018.

TECHNICAL FIELD

The invention relates to methods for producing a cyclic carbonate containing an unsaturated group and novel cyclic carbonates.

BACKGROUND ART

Cyclic carbonates such as ethylene carbonate and propylene carbonate are widely used as plastic materials, solvents, and the like. They are very important compounds as functional materials, chemical products such as pharmaceutical or agrochemical compounds, and intermediates thereof. Development of novel cyclic carbonate compounds is always awaited.

Examples of conventionally known methods for adding a group such as an alkoxy group to a side chain of ethylene carbonate include formation of a cyclic carbonate using an epoxide containing an alkoxy group and $CO_2$, a method of reacting chloroethylene carbonate with an alkoxide, and a method of adding an alcohol containing a fluorine atom to vinylene carbonate (for example, see Patent Literature 1).

CITATION LIST

Patent Literature

Patent Literature 1: WO 2017/017210

SUMMARY OF INVENTION

Technical Problem

No method for easily and simply producing a cyclic carbonate containing an unsaturated group has been known.

The invention aims to provide a method for easily and simply producing a cyclic carbonate containing an unsaturated group. The invention also aims to provide a novel cyclic carbonate.

Solution to Problem

The inventors examined a method for easily and simply producing a cyclic carbonate containing an unsaturated group and found that a vinylene carbonate compound and a specific compound containing an unsaturated group selectively react with each other, enabling easy and simple production of a cyclic carbonate containing an unsaturated group. Thereby, the inventors completed the invention.

In other words, the invention relates to a method for producing a cyclic carbonate represented by the following formula (1):

[Chem. 1]

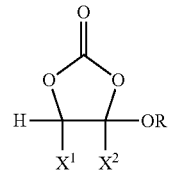
(1)

wherein $X^1$ and $X^2$ are the same as or different from each other, and are each a hydrogen atom, a fluorine atom, or a monovalent organic group; and R is an organic group containing one or more carbon-carbon unsaturated bonds, the method including
reacting an unsaturated cyclic carbonate represented by the following formula (A):

[Chem. 2]

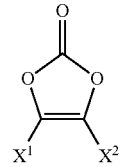
(A)

wherein $X^1$ and $X^2$ are defined as described above, and an alcohol represented by the following formula (B):

$$R\text{—}OH \quad (B)$$

wherein R is defined as described above, or an alkoxide thereof in the presence of a base, or reacting the unsaturated cyclic carbonate and the alkoxide.

$X^1$ and $X^2$ are the same as or different from each other, and are each preferably a hydrogen atom, a fluorine atom, or an alkyl, aryl, alkoxyalkyl, or aryloxyalkyl group optionally containing a fluorine atom.

R is preferably a C1-C10 alkyl group containing one or more carbon-carbon unsaturated bonds and optionally containing one or both selected from a divalent or higher heteroatom and a fluorine atom.

R is preferably
a group represented by the following formula (C):

$$\text{—}(R^{b1})\text{—}C\!\equiv\!C\text{-}L^1 \quad (C)$$

wherein $R^{b1}$ is an alkylene group optionally containing an oxygen atom or an unsaturated bond between carbon atoms; and $L^1$ is a hydrogen atom, a fluorine atom, a C1-C7 silyl or aryl group optionally containing a fluorine atom, or a C1-C7 alkyl group optionally containing one or both selected from a divalent or higher heteroatom and a fluorine atom,
a group represented by the following formula (D):

$$\text{—}(R^{b2})\text{—}CL^2\!=\!CL^3L^4 \quad (D)$$

wherein $R^{b2}$ is a single bond or an alkylene group optionally containing an oxygen atom or an unsaturated bond between carbon atoms; $L^2$, $L^3$, and $L^4$ are the same as or different from each other, and are each a hydrogen atom, a fluorine atom, a C1-C8 silyl group optionally containing a fluorine atom, or a C1-C8 alkyl or aryl group optionally containing one or both selected from a divalent or higher heteroatom and a fluorine atom; and at least one selected from $L^2$, $L^3$, and $L^4$ contains a fluorine atom, or a group represented by the following formula (E):

wherein $R^{b2}$ is defined as described above; and $L^5$ is a group containing an aromatic ring.

R is also preferably a C1-C10 alkyl group containing a divalent or higher heteroatom and one or more carbon-carbon unsaturated bonds. The divalent or higher heteroatom is preferably an oxygen atom or a silicon atom.

The base preferably includes at least one selected from the group consisting of a hydride of an alkali metal or an alkaline earth metal, a hydroxide of an alkali metal or an alkaline earth metal, a carbonate compound of an alkali metal or an alkaline earth metal, a hydrogencarbonate compound of an alkali metal, an alkoxide of an alkali metal or an alkaline earth metal, an amide of an alkali metal or an alkaline earth metal, guanidine, and an amine.

The invention also relates to a cyclic carbonate represented by the following formula (1a):

[Chem. 3]

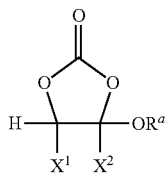

(1a)

wherein $X^1$ and $X^2$ are the same as or different from each other, and are each a hydrogen atom, a fluorine atom, or a monovalent organic group; and $R^a$ is a monovalent organic group containing one or more carbon-carbon triple bonds or a monovalent organic group containing a fluorine atom and one or more carbon-carbon unsaturated bonds.

$X^1$ and $X^2$ are the same as or different from each other, and are each preferably a hydrogen atom, a fluorine atom, or an alkyl, aryl, alkoxyalkyl, or aryloxyalkyl group optionally containing a fluorine atom.

$R^a$ is preferably a C1-C10 alkyl group optionally containing one or both selected from a divalent or higher heteroatom and a fluorine atom.

$R^a$ is preferably a group represented by the following formula (C):

wherein $R^{b1}$ is an alkylene group optionally containing an oxygen atom or a carbon-carbon unsaturated bond between carbon atoms; and $L^1$ is a hydrogen atom, a fluorine atom, a C1-C7 silyl or aryl group optionally containing a fluorine atom, or a C1-C7 alkyl group optionally containing one or both selected from a divalent or higher heteroatom and a fluorine atom, a group represented by the following formula (D):

wherein $R^{b2}$ is a single bond or an alkylene group optionally containing an oxygen atom or an unsaturated bond between carbon atoms; $L^2$, $L^3$, and $L^4$ are the same as or different from each other, and are each a hydrogen atom, a fluorine atom, a C1-C8 silyl group optionally containing a fluorine atom, or a C1-C8 alkyl or aryl group optionally containing one or both selected from a divalent or higher heteroatom and a fluorine atom; and at least one selected from $L^2$, $L^3$, and $L^4$ contains a fluorine atom, or a group represented by the following formula (E'):

wherein $R^{b2}$ is defined as described above; $L^{5a}$ is a group containing an aromatic ring; and $L^{5a}$ contains a fluorine atom.

$R^a$ is also preferably a C10 or lower alkyl group containing a divalent or higher heteroatom and one or more carbon-carbon unsaturated bonds. The divalent or higher heteroatom is preferably an oxygen atom or a silicon atom.

Advantageous Effects of Invention

The production method of the invention enables easy and simple production of a cyclic carbonate containing an unsaturated group. The novel cyclic carbonate of the invention is a very important compound as any of a variety of chemicals such as pharmaceutical or agrochemical compounds and intermediates thereof.

DESCRIPTION OF EMBODIMENTS

The invention relates to a method for producing a cyclic carbonate represented by the formula (1), including reacting an unsaturated cyclic carbonate represented by the formula (A) and an alcohol represented by the formula (B) or an alkoxide thereof in the presence of a base, or reacting the unsaturated cyclic carbonate and the alkoxide.

$X^1$ and $X^2$ are the same as or different from each other, and are each a hydrogen atom, a fluorine atom, or a monovalent organic group.

The "organic group" as used herein means a group containing at least one carbon atom, and may contain an atom other than the carbon atom, such as a hydrogen atom, an oxygen atom, a nitrogen atom, a sulfur atom, or a halogen atom (e.g., a fluorine atom, a chlorine atom).

In $X^1$ and $X^2$, examples of the organic group include an alkyl group optionally containing at least one substituent, a cycloalkyl group optionally containing at least one substituent, a vinyl group, an aryl group, an alkynyl group, and an alkenyl group.

Examples of the substituent include a halogen atom, preferably a fluorine atom, an alkyl group, a fluorinated alkyl group, and a group containing a heteroatom. Preferred is a halogen atom, more preferred is a fluorine atom.

The group containing a heteroatom may be a group containing a nitrogen atom, an oxygen atom, or a sulfur atom. Examples thereof include an amino group, a hydroxy group, an ether bond, an ester bond, a thiol bond, and a —SH group.

The number of substituents is preferably, but not limited to, 0 to 4, more preferably 1 to 4, still more preferably 1 to 3, particularly preferably 1 or 2.

The organic group preferably has a carbon number of 1 to 10, more preferably 1 to 6.

$X^1$ and $X^2$ are the same as or different from each other, and are each preferably a hydrogen atom, a fluorine atom, or an alkyl, aryl, alkoxyalkyl, or aryloxyalkyl group optionally containing a fluorine atom.

The alkyl group optionally containing a fluorine atom preferably has a carbon number of 1 to 10, more preferably 1 to 7, still more preferably 1 to 5.

Examples of an alkyl group free from a fluorine atom include a methyl group, an ethyl group, a propyl group, an isopropyl group, a butyl group, a t-butyl (t-Bu) group, a sec-butyl group, a pentyl group, an isopentyl group, a hexyl group, and a cyclohexyl group. Preferred is at least one selected from the group consisting of a methyl group, an ethyl group, a propyl group, an isopropyl group, a butyl group, a t-butyl group, and a sec-butyl group.

Examples of an alkyl group containing a fluorine atom include a trifluoromethyl group, a 2,2,2-trifluoroethyl group, a 2,2,3,3-tetrafluoropropyl group, 1,1,1,3,3,3-hexafluoropropan-2-yl, $CF_3CF_2CH_2$—, $HCF_2CH_2$—, $FCH_2$—, and $FCH_2CH_2$—. Preferred is at least one selected from the group consisting of a trifluoromethyl group, a 2,2,2-trifluoroethyl group, and a 2,2,3,3-tetrafluoropropyl group.

The terms "t-Bu" and "sec-butyl group" as used herein respectively mean a tertiary butyl group and a secondary butyl group.

Examples of the aryl group optionally containing a fluorine atom include a phenyl group, a monofluorophenyl group, a difluorophenyl group, and a tetrafluorophenyl group.

The alkoxyalkyl group optionally containing a fluorine atom preferably has a carbon number of 2 to 10, more preferably 2 to 7, still more preferably 2 to 5.

Examples of an alkoxyalkyl group free from a fluorine atom include —$CH_2OCH_3$, —$CH_2CH_2OCH_3$, —$CH_2OCH_2CH_3$, and —$CH_2CH_2OCH_2CH_3$. Preferred is at least one selected from the group consisting of —$CH_2OCH_3$ and —$CH_2CH_2OCH_3$.

Examples of an alkoxyalkyl group containing a fluorine atom include groups represented by the following formula:

$$R^2OR^3—$$

wherein $R^2$ is —$CF_3$, —$CH_2CF_3$, $CH_2CH_2CF_3$, $CH_2CF_2CF_3$—$CH(CF_3)_2$, —$CH_2CF_2CF_2H$, —$CH_2CF_2H$, —$CH_2CH_2F$, or —$CF_2CF_2H$; and $R^3$ is —$CH_2CH_2$—, —$CH_2$—, or —$CH_2CF_2$—.

Specific examples thereof include —$CH_2OCF_3$, —$CH_2CH_2OCF_3$, —$CH_2CF_2OCF_3$, —$CH_2OCH_2CF_3$, —$CH_2CH_2OCH_2CF_3$, $CH_2CF_2OCH_2CF_3$, —$CH_2OCH_2CF_2CF_3$, —$CH_2CH_2OCH_2CF_2CF_3$, —$CH_2CF_2OCH_2CF_2CF_3$, —$CH_2OCH(CF_3)_2$, —$CH_2CH_2OCH(CF_3)_2$, —$CH_2CF_2OCH(CF_3)_2$, —$CH_2OCH_2CF_2H$, —$CH_2CH_2OCH_2CF_2H$, —$CH_2CF_2OCH_2CF_2H$, —$CH_2OCH_2CF_2CF_2H$, —$CH_2CH_2OCH_2CF_2CF_2H$, —$CH_2CF_2OCH_2CF_2CF_2H$, —$CH_2OCH_2CH_2F$, —$CH_2CH_2OCH_2CH_2F$, —$CH_2CF_2OCH_2CH_2F$, —$CH_2OCF_2CF_2H$, —$CH_2CH_2OCF_2CF_2H$, and —$CH_2CF_2OCF_2CF_2H$.

Preferred is at least one selected from the group consisting of —$CH_2OCF_3$ and —$CH_2CH_2OCF_3$.

Examples of the aryloxyalkyl group optionally containing a fluorine atom include C7-C12 aryloxy groups. At least one hydrogen atom in these aryloxy groups may be replaced by a fluorine atom.

When $X^1$ is a substituent other than a hydrogen atom, the cyclic carbonate represented by the formula (1) includes a stereoisomer. When including a stereoisomer, the cyclic carbonate may be a mixture containing a cis form and a trans form at any ratio or may be a compound represented by one of these structures.

R is an organic group containing one or more carbon-carbon unsaturated bonds. Each carbon-carbon unsaturated bond is preferably a carbon-carbon double bond (—C=C—) or a carbon-carbon triple bond (—C≡C—). When a carbon-carbon double bond is present, the substituents binding to the carbon-carbon double bond may form either an E-form geometrical isomer or a Z-form geometrical isomer, or may form a mixture thereof at any ratio.

The organic group for R preferably has a carbon number of 2 to 10, more preferably 2 to 7, still more preferably 2 to 5.

R is preferably a C1-C10 alkyl group containing one or more carbon-carbon unsaturated bonds and optionally containing one or both selected from a divalent or higher heteroatom and a fluorine atom. The alkyl group preferably has a carbon number of 1 to 8, more preferably 1 to 7, still more preferably 1 to 5.

In R, the heteroatom is preferably divalent, trivalent, or tetravalent.

Examples of the divalent or higher heteroatom include a nitrogen atom, an oxygen atom, a sulfur atom, a phosphorus atom, and a silicon atom.

R is preferably
a group represented by the following formula (C):

$$—(R^{b1})—C≡C-L^1 \quad (C)$$

wherein $R^{b1}$ is an alkylene group optionally containing an oxygen atom or an unsaturated bond between carbon atoms; and $L^1$ is a hydrogen atom, a fluorine atom, a C1-C7 silyl or aryl group optionally containing a fluorine atom, or a C1-C7 alkyl group optionally containing one or both selected from a divalent or higher heteroatom and a fluorine atom;

a group represented by the following formula (D):

$$—(R^{b2})—CL^2=CL^3L^4 \quad (D)$$

wherein $R^{b2}$ is a single bond or an alkylene group optionally containing an oxygen atom or an unsaturated bond between carbon atoms; $L^2$, $L^3$, and $L^4$ are the same as or different from each other, and are each a hydrogen atom, a fluorine atom, a C1-C8 silyl group optionally containing a fluorine atom, or a C1-C8 alkyl or aryl group optionally containing one or both selected from a divalent or higher heteroatom and a fluorine atom; and at least one selected from $L^2$, $L^3$, and $L^4$ contains a fluorine atom; or a group represented by the following formula (E):

$$—(R^{b2})-L^5 \quad (E)$$

wherein $R^{b2}$ is defined as described above; and $L^5$ is a group containing an aromatic ring.

In the formula (D), the substituents binding to the carbon-carbon double bond may form either an E-form geometrical isomer or a Z-form geometrical isomer, or may form a mixture thereof at any ratio.

Examples of the alkyl group for $L^1$ include —$CF_3$, —$CF_2CF_3$, —$CH_3$, and —$CH_2CH_3$.

The silyl group for $L^1$ may be a group represented by the formula: —$SiR^bR^cR^d$, wherein $R^b$, $R^c$, and $R^d$ are the same as or different from each other, and are each a C1-C5 alkyl group optionally containing a fluorine atom.

Specific examples of $L^1$ include a hydrogen atom, a fluorine atom, —$CH_3$, —$CH_2CH_3$, —$CF_3$, —$CF_2CF_3$, —Si$(CH_3)_2$ $(C_4H_9)$, —Si$(CH_3)_3$, and —Si$(CH_3)_2$(t-Bu). Preferred is at least one selected from the group consisting of a hydrogen atom, a fluorine atom, —Si$(CH_3)_3$, —$CF_3$, —$CF_2CF_3$, a phenyl group, and a perfluorophenyl group.

$R^{b1}$ preferably has a carbon number of 1 to 8. $R^{b1}$ is preferably a group represented by —$(CH_2)_{n1}$— (wherein n1 is an integer of 1 to 8). In the formula, n1 is preferably 1 to 5, more preferably 1 to 3.

Examples of the alkyl group and the aryl group for $L^2$, $L^3$, and $L^4$ include —$CF_3$, —$CH_3$, —$CF_2CF_3$, a phenyl group, and a perfluorophenyl group.

The silyl group for $L^2$, $L^3$, and $L^4$ may be a group represented by the formula: —$SiR^bR^cR^d$, wherein $R^b$, $R^c$, and $R^d$ are the same as or different from each other, and are each a C1-C5 alkyl group optionally containing a fluorine atom.

At least one selected from $L^2$, $L^3$, and $L^4$ contains a fluorine atom. This can give improved oxidation resistance and durability to a cyclic carbonate to be produced.

Specific examples of $L^2$, $L^3$, and $L^4$ include a hydrogen atom, a fluorine atom, —$CH_3$, —$CH_2CH_3$, $CF_3$, $CF_2CF_3$, $Si(CH_3)_2$(t-Bu), and —$Si(CH_3)_3$. Preferred is at least one selected from the group consisting of a hydrogen atom, —$CH_3$, —$CF_3$, a fluorine atom, a phenyl group, and a perfluorophenyl group.

$L^5$ is a group containing an aromatic ring. Specific examples of $L^5$ include a phenyl group and a perfluorophenyl group. A preferred group represented by the formula (E) may be an aryl group.

$R^{b2}$ preferably has a carbon number of 0 to 8. $R^{b2}$ is preferably a group represented by —$(CH_2)_{n2}$— (wherein n2 is an integer of 0 to 8). In the formula, n2 is preferably 0 to 5, more preferably 1 to 3.

R is also preferably a C1-C10 alkyl group containing a divalent or higher heteroatom and one or more carbon-carbon unsaturated bonds.

Examples of the divalent or higher heteroatom include a nitrogen atom, an oxygen atom, a sulfur atom, a phosphorus atom, and a silicon atom. Preferred among these is an oxygen atom or a silicon atom.

Examples of the alkyl group containing a divalent or higher heteroatom and one or more carbon-carbon unsaturated bonds include —O—$CH_2$—CH=CH—$Si(CH_3)_2$(t-Bu) and —$OCH_2$—CH=CH—$Si(CH_3)_3$.

The compound represented by the formula (1) is preferably a cyclic carbonate represented by the following formula (1-1):

[Chem. 4]

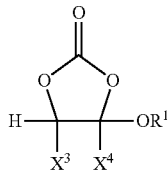

wherein $X^3$ and $X^4$ are the same as or different from each other, and are each —H, —F, —$CH_3$, —$C_2H_5$, —$C_3H_7$, —$C_4H_9$, —$CF_3$, —$O_2F_5$, —$O_3F_7$, or —$O_4F_9$; and $R^1$ is —$CH_2$—CH=$CH_2$, —$CH_2$—CF=$CH_2$, $CH_2$—CH=$CH_2$—$CF_3$, —$CH_2$—CH=$CF_2$, —$CH_2$—CF=$CF_2$, —$CH_2$—CF=CF—$CF_3$, $CH_2$—CH=CF—$CF_3$, —$CH_2$—CH=CF—$Si(CH_3)_2$(tBu), —$CH_2$—CF=CF—$Si(CH_3)_2$(tBu), —$CH_2$—C≡C—$Si(CH_3)_2$(tBu), —$CH_2$—C≡C-TMS, —$CH_2$—C≡C—$CF_3$, —$CH_2$—C≡C—F, a phenyl group, or a perfluorophenyl group).

In the formula, -TMS means a trimethylsilyl group.

When $R^1$ is a group containing a carbon-carbon double bond and $X^3$ and $X^4$ are both —H in the formula (1-1), $R^1$ preferably contains a fluorine atom.

When $X^3$ is a substituent other than a hydrogen atom in the formula (1-1), the cyclic carbonate represented by the formula (1-1) includes a stereoisomer. When including a stereoisomer, the cyclic carbonate may be a mixture containing a cis form and a trans form at any ratio or may be a compound represented by one of these structures.

When $R^1$ contains a carbon-carbon double bond, the substituents binding to the carbon-carbon double bond may form either an E-form geometrical isomer or a Z-form geometrical isomer, or may form a mixture thereof at any ratio.

$X^3$ and $X^4$ each may be either a group containing a fluorine atom or a group free from a fluorine atom. In order to achieve good stability of the compound, preferred is a group free from a fluorine atom. In order to achieve good oxidation resistance of the compound, a group containing a fluorine atom is also preferred.

$X^3$ and $X^4$ are each preferably a C1-C4 group, more preferably a C1-C3 group.

$X^3$ and $X^4$ are the same as or different from each other, and are each preferably —H, —$CH_3$, —F, or —$CF_3$, more preferably —H, —$CH_3$, or —$CF_3$.

$R^1$ is preferably —$CH_2$—CH=$CH_2$, —$CH_2$—C≡CH, —$CH_2$—CF=$CH_2$, or —$CH_2CH$=CH—$CF_3$, more preferably —$CH_2$—CH=$CH_2$, —$CH_2$—C≡CH, or —$CH_2$—CF=$CH_2$.

In terms of polymerizability of the compound, $R^1$ is preferably a group containing a carbon-carbon double bond. In terms of crystallizability of the compound, preferred is a group containing a carbon-carbon triple bond.

Specific examples of the compound represented by the formula (1) include compounds represented by the following formulas. When the compounds represented by the following formulas include stereoisomers such as geometrical isomers, each of the stereoisomers and mixtures of two or more of these stereoisomers are also included in the examples. The compound represented by the formula (1) is not limited to the compounds represented by the following formulas.

[Chem. 5]

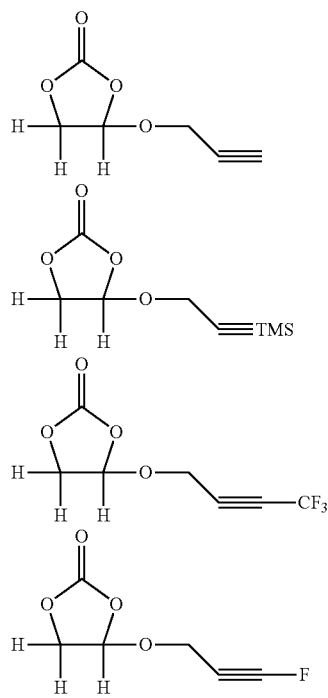

[Chem. 6]
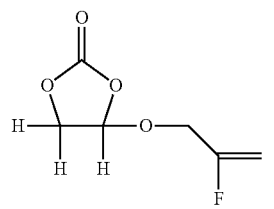
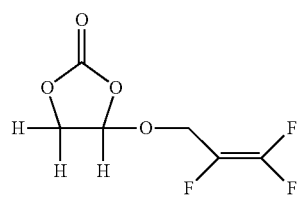
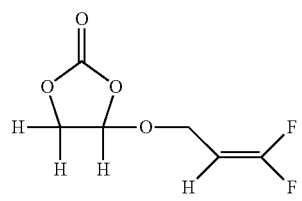
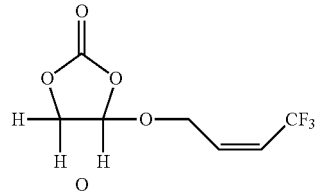
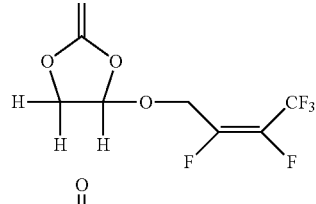
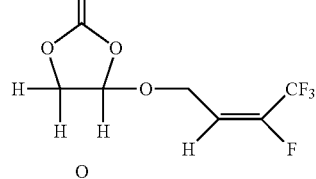
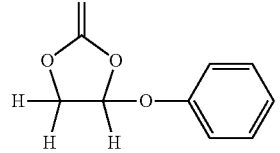
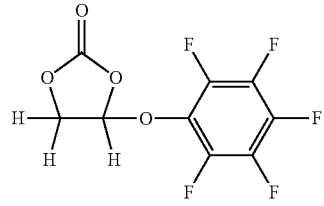
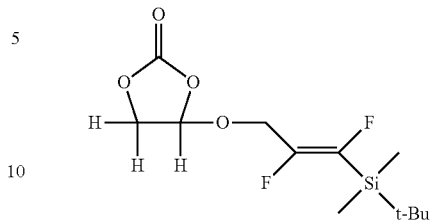
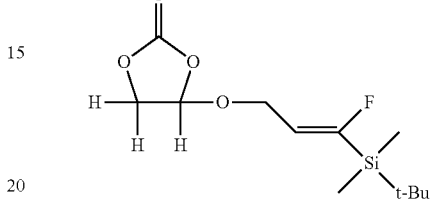
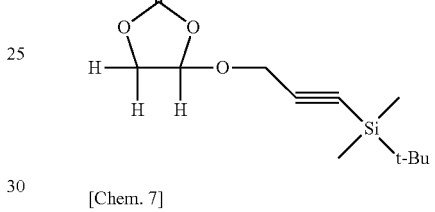
[Chem. 7]
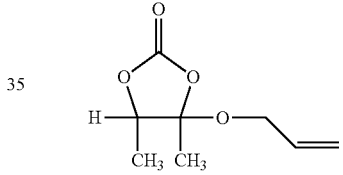
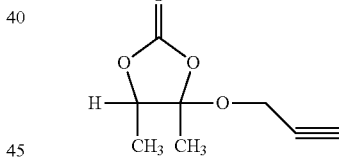
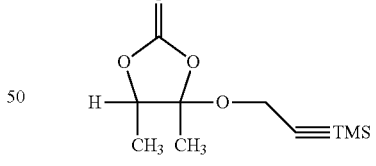
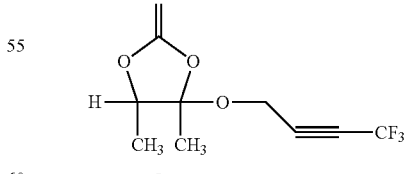
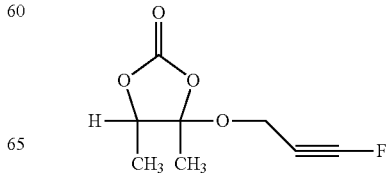

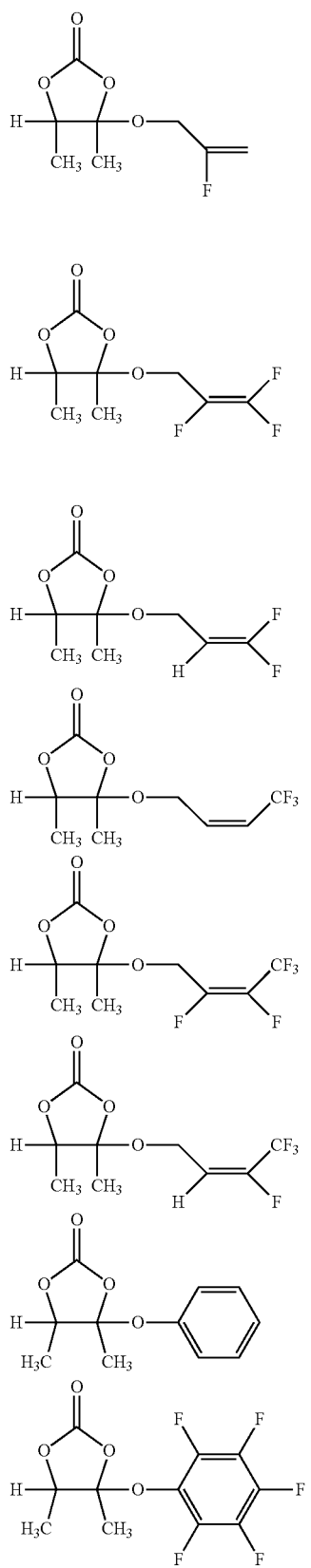
[Chem. 8]
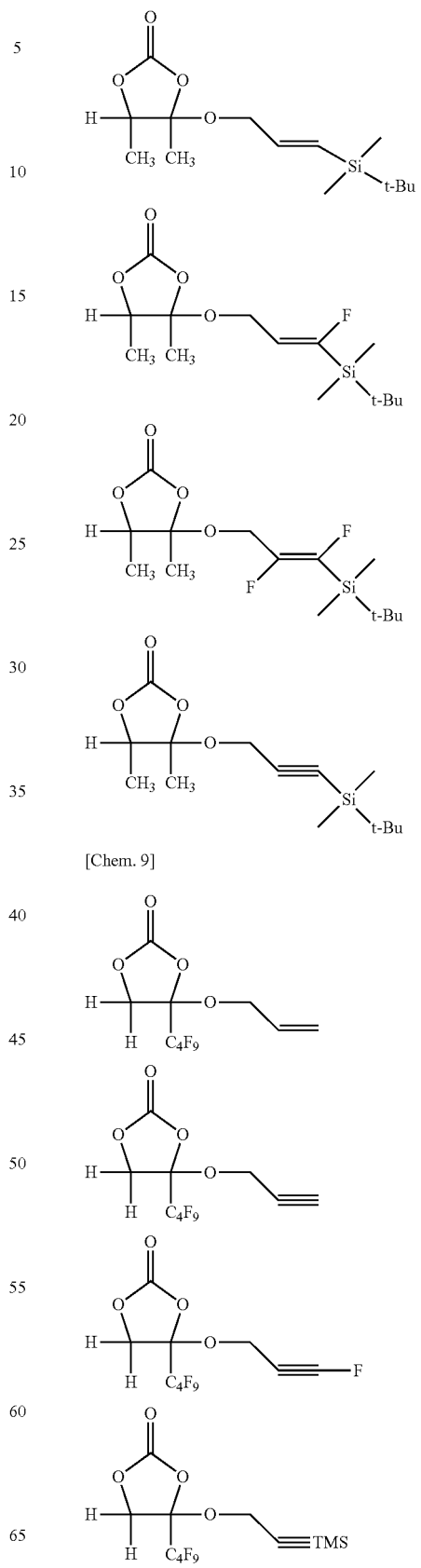
[Chem. 9]
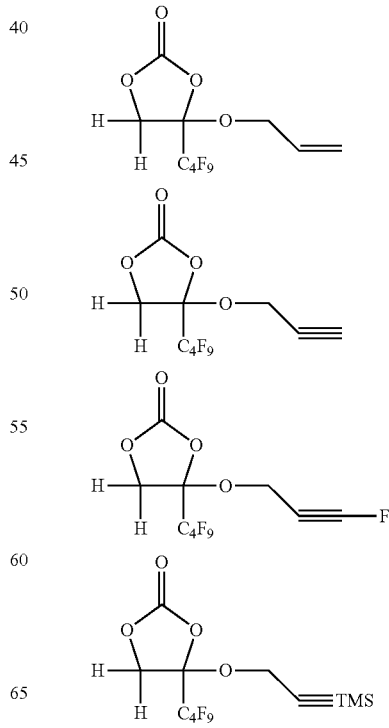

-continued
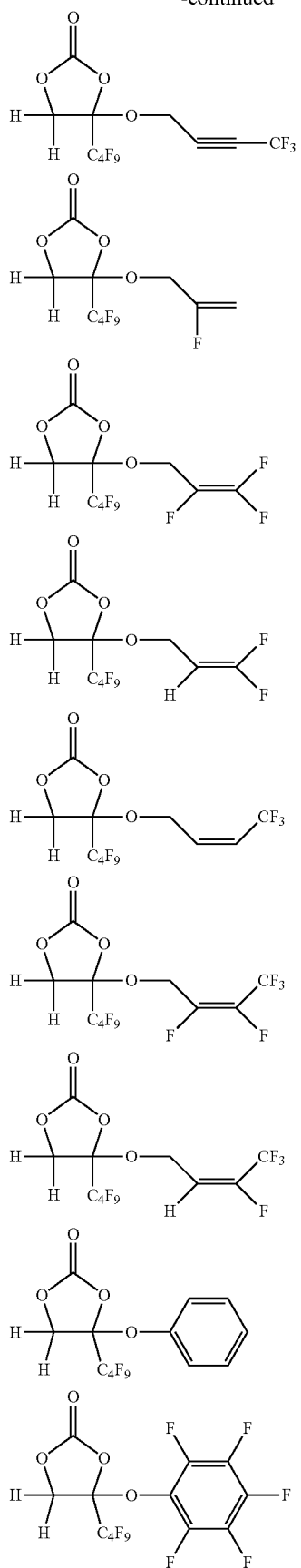
-continued
[Chem. 10]
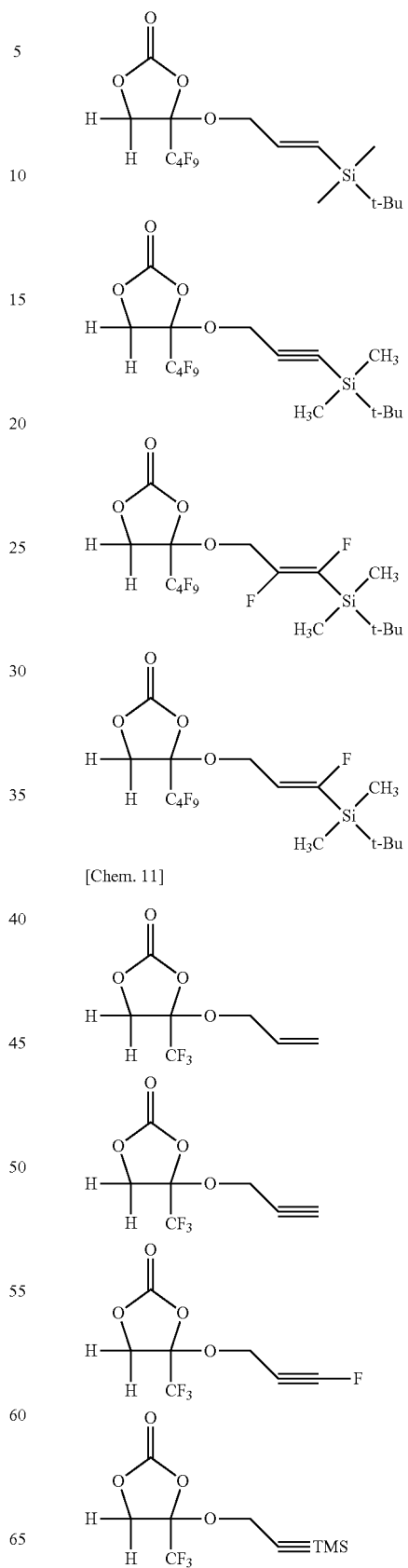
[Chem. 11]

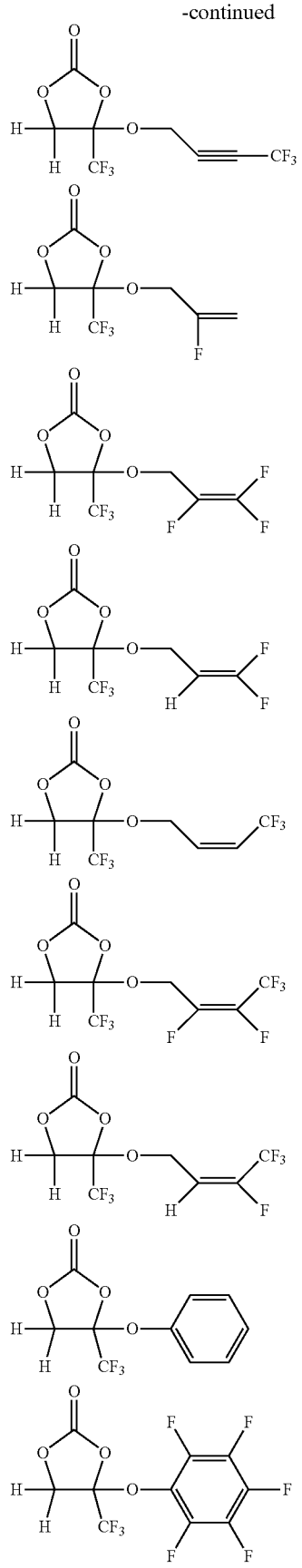
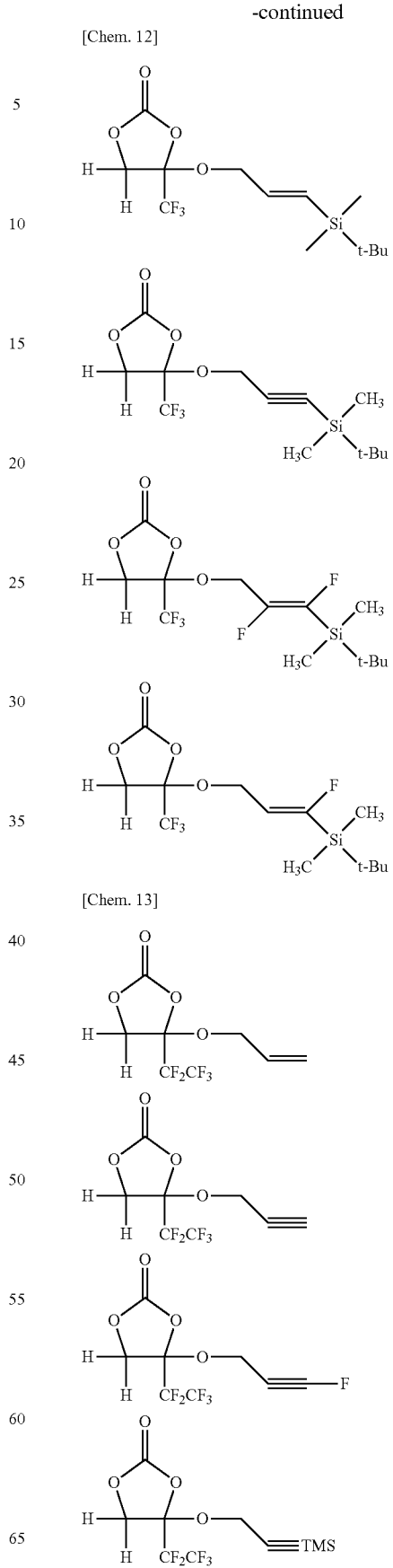

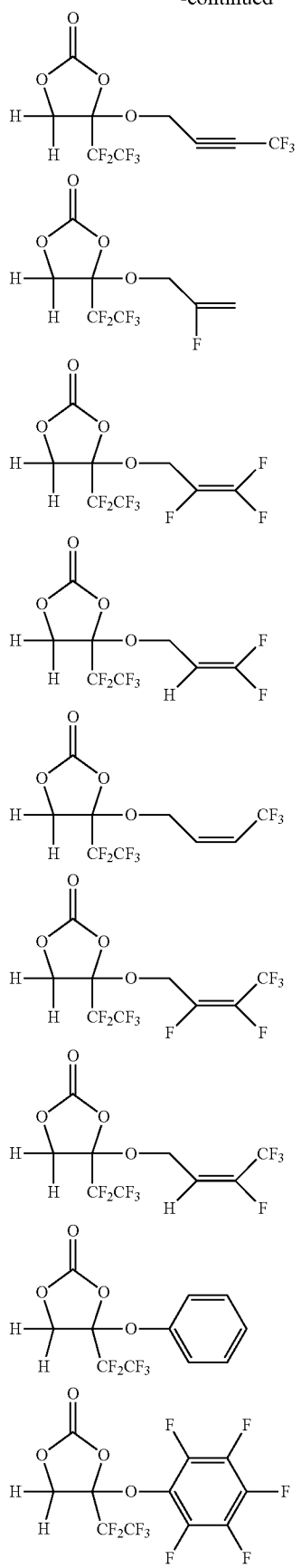
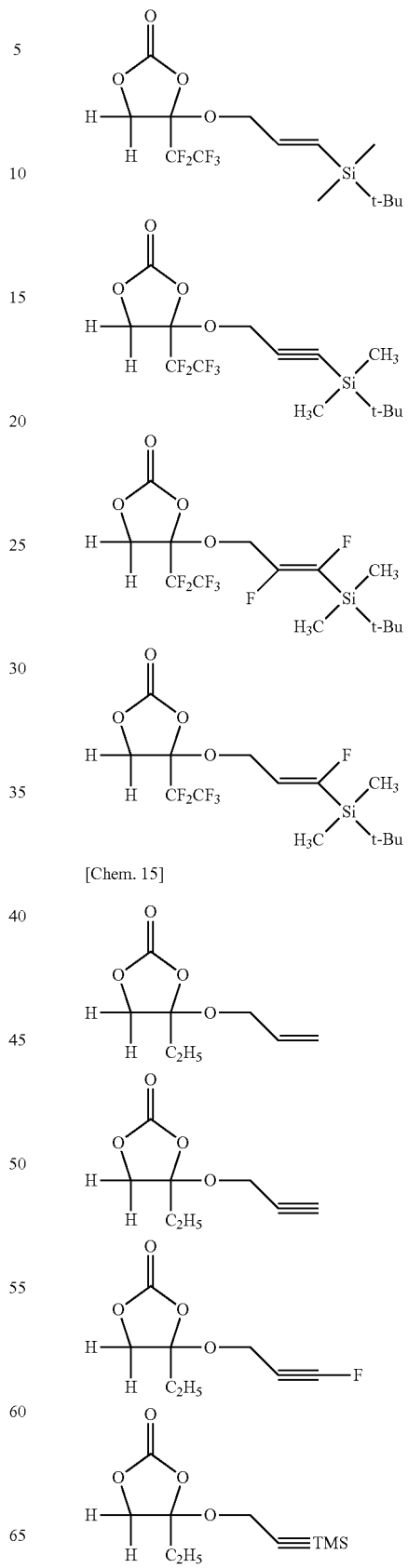

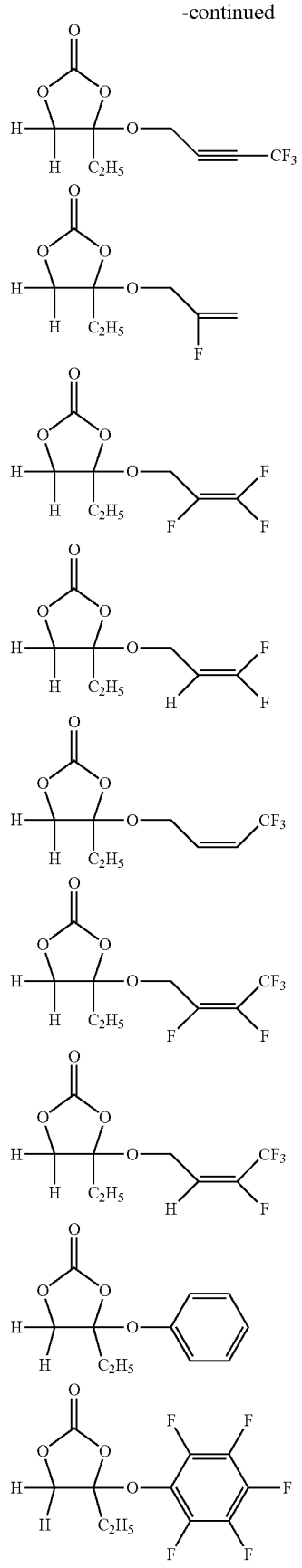
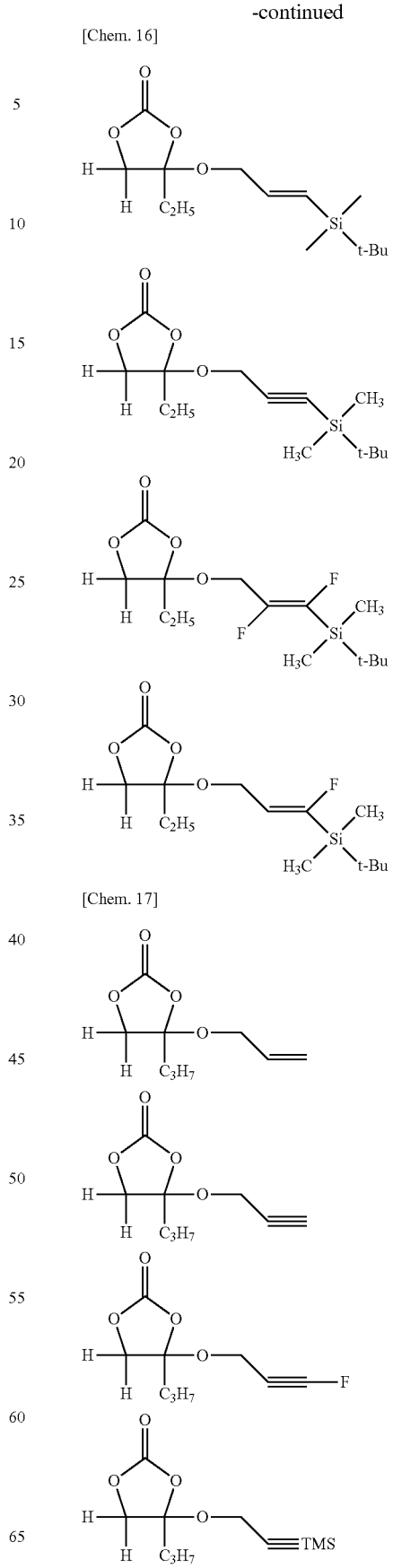

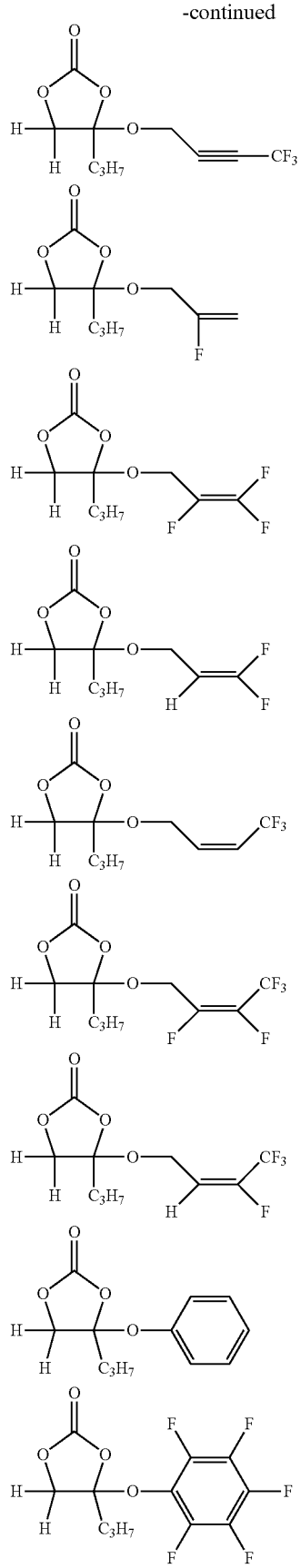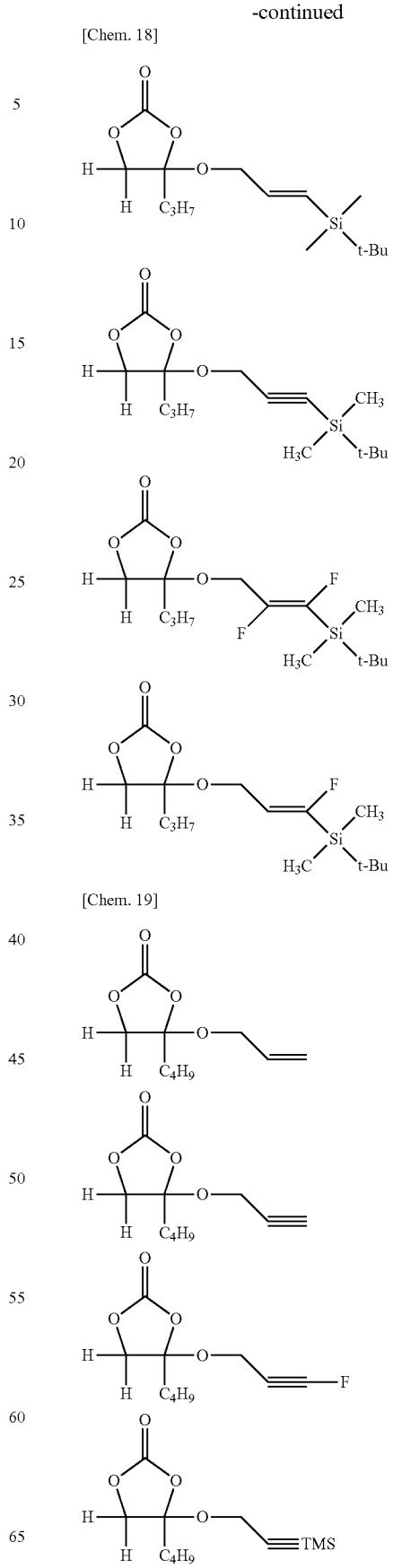

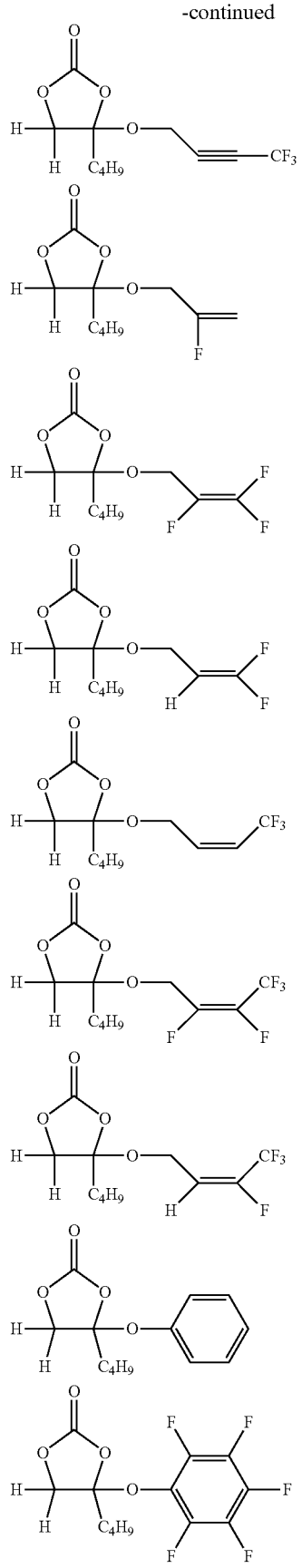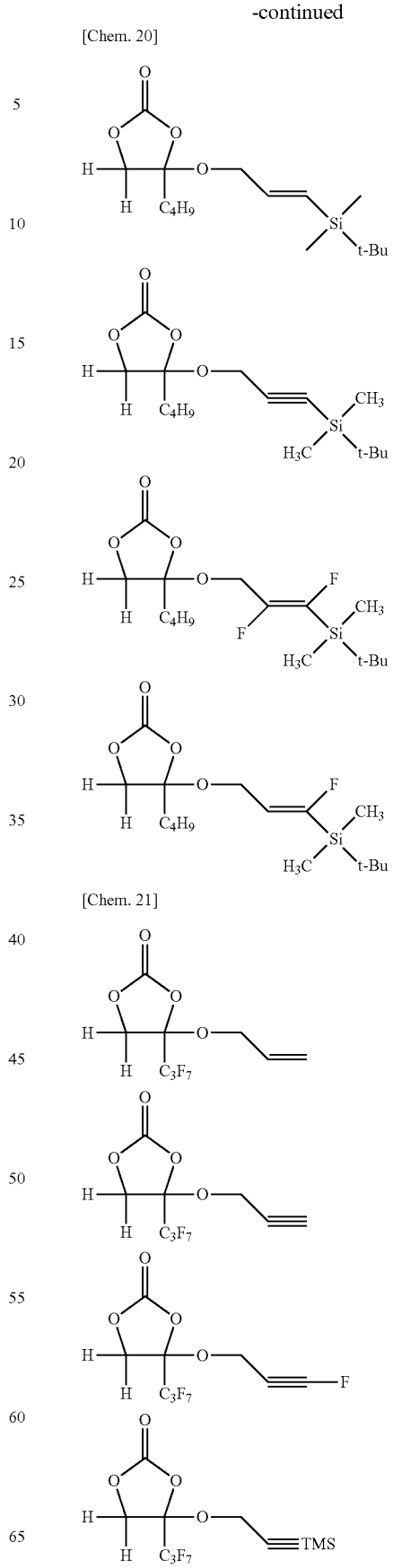

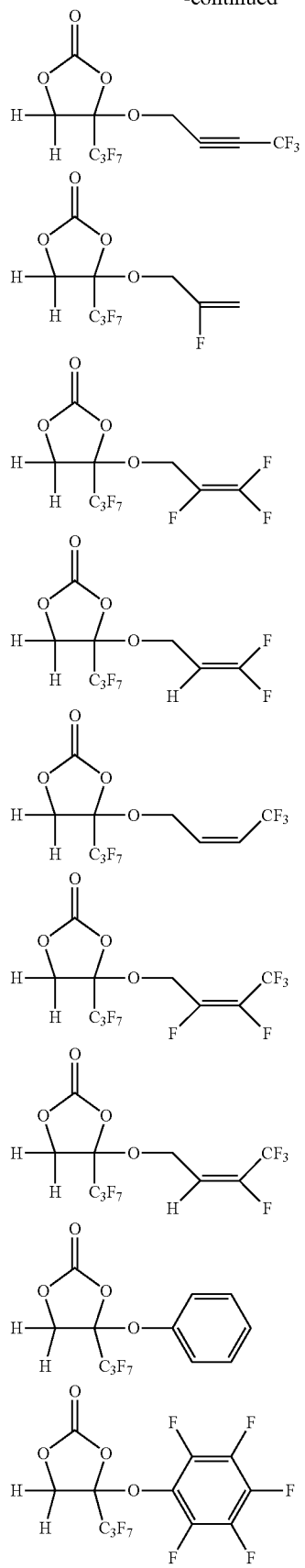
[Chem. 22]
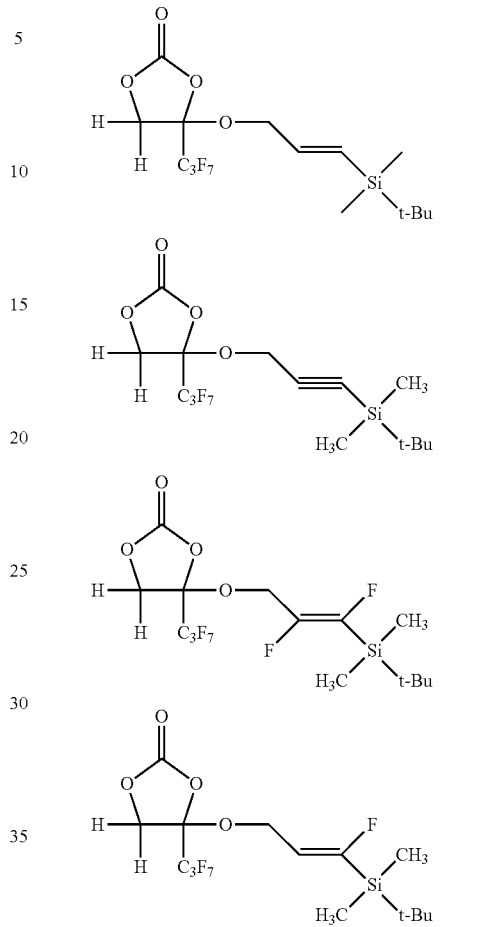
Specific examples of the compound represented by the formula (A) include compounds represented by the following formulas.
[Chem. 23]
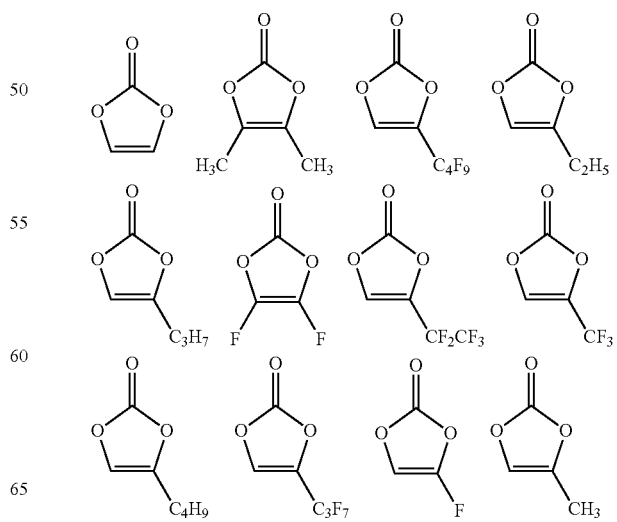

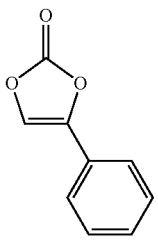

Specific examples of the alcohol represented by the formula (B) include CH≡C—CH₂—OH, CH₂=CH—CH₂—OH, CH₂=CFCH₂—OH, CF₃—CH=CH—CH₂—OH, Si(CH₃)₂ (t-Bu)-CH=CH—CH₂—OH, CF₂=CF—CH₂—OH, CF₂=CH—CH₂—OH, CF₃—CF=CF—CH₂—OH, CF₃—CF=CH—CH₂—OH, Si(CH₃)₂(t-Bu)-CF=CH—CH₂—OH, Si(CH₃)₂(t-Bu)-CF=CF—CH₂—OH, TMS—C≡C—CH₂—OH, CF₃—C≡C—CH₂—OH, CF≡C—CH₂—OH, Si(CH₃)₂(t-Bu)-C≡C—CH₂—OH, a phenol, and pentafluorophenol.

Preferred among these is at least one selected from the group consisting of CH≡C—CH₂—OH, CH₂=CH—CH₂—OH, CH₂=CFCH₂—OH, CF₃—CH=CH—CH₂—OH, and a phenol.

Examples of an alkoxide of the alcohol represented by the formula (B) include an ammonium alkoxide and a metal alkoxide of any of the above alcohols. The metal alkoxide may be either an alkoxide of a monovalent metal or an alkoxide of a divalent metal. Examples thereof include alkoxides of metals such as lithium, sodium, potassium, magnesium, calcium, and caesium.

The production method of the invention includes reacting an unsaturated cyclic carbonate represented by the formula (A) and an alcohol represented by the formula (B) or an alkoxide thereof in the presence of a base, or reacting the unsaturated cyclic carbonate and the alkoxide (hereinafter, this is referred to as a "reaction step").

The base may be, but not limited to, either an inorganic base or an organic base.

The base may either a weak base or a strong base, and is preferably a strong base. A strong base enables more smooth progress of the reaction step.

In the case of reacting the unsaturated cyclic carbonate represented by the formula (A) and an alkoxide of the alcohol represented by the formula (B), the reaction can progress even without the base. Thus, the reaction may be performed in the presence of the base or in the absence of the base.

The base preferably includes at least one selected from the group consisting of a hydride of an alkali metal or an alkaline earth metal, a hydroxide of an alkali metal or an alkaline earth metal, a carbonate compound of an alkali metal or an alkaline earth metal, a hydrogencarbonate compound of an alkali metal, an alkoxide of an alkali metal or an alkaline earth metal, an amide of an alkali metal or an alkaline earth metal, guanidine, and an amine.

Examples of the hydride include NaH, LiH, and CaH₂.

Examples of the hydroxide include LiOH, KOH, NaOH, Ca(OH)₂, Ba(OH)₂, Mg(OH)₂, Cu(OH)₂, Al(OH)₃, and Fe(OH)₃.

Examples of the carbonate compound include K₂CO₃, Na₂CO₃, CaCO₃, and CsCO₃.

Examples of the hydrogencarbonate compound include NaHCO₃ and KHCO₃.

Examples of the alkoxide include potassium methoxide, potassium ethoxide, potassium propoxide, potassium butoxide, sodium methoxide, sodium ethoxide, sodium propoxide, and sodium butoxide.

Examples of the amine include triethylamine, diisopropylethylamine, tributylamine, ethyldiisopropylamine, pyridine, imidazole, N-methylimidazole, N,N'-dimethylaminopyridine, picoline, 1,5-diazabicyclo[4.3.0]non-5-ene (DBN), 1,4-diazabicyclo[2.2.2]octane (DABCO), and 1,8-diazabicyclo[5.4.0]undec-7-ene (DBU).

Examples of the amide include sodium amide and lithium diisopropylamide.

The base preferably includes at least one selected from the group consisting of NaH, LiH, guanidine, and an amine, more preferably at least one selected from the group consisting of NaH and an amine.

Bases such as butyllithium and N-methylmorpholine may also be used.

The base used in the reaction step is preferably in an amount of 0.01 to 1.1 equivalents based on the amount of the cyclic carbonate represented by the formula (A).

The base may be used in an excess amount. The amount of the base is preferably 1 to 25 mol % or less, more preferably 1 to 10 mol % or less, still more preferably 1 to 6 mol %, based on the amount of the cyclic carbonate represented by the formula (A).

In the reaction step, the alcohol represented by the formula (B) or an alkoxide thereof is preferably in an amount of 0.9 to 1.1 equivalents based on the cyclic carbonate represented by the formula (A).

The alcohol represented by the formula (B) or an alkoxide thereof may be used in an excess amount. The alcohol or an alkoxide thereof is preferably in an amount of 1 to 20 equivalents, more preferably 1.1 to 10 equivalents, based on the cyclic carbonate represented by the formula (A).

The reaction step may be performed in the presence of a solvent other than the alcohol represented by the formula (B). The solvent is preferably an aprotic solvent. Examples thereof include tetrahydrofuran, monoglyme, diethyl alkoxyalkylene, and acetonitrile.

In the production method of the invention, the alcohol represented by the formula (B) can also be used as a solvent. Thus, the reaction can progress even without the solvent other than the alcohol represented by the formula (B).

The temperature in the reaction step is preferably 20° C. or lower, more preferably 5° C. or lower, while preferably 0° C. or higher.

The reaction duration may be, but is not limited to, 60 to 240 minutes, for example.

The mixture obtained in the reaction step may be separated into the respective components by a known technique such as coagulation or crystallization.

The method for producing a cyclic carbonate of the invention can easily and simply provide a cyclic carbonate containing an unsaturated group by a selective reaction of a vinylene carbonate compound and a specific compound containing an unsaturated group. Progress of such a selective reaction can lead to production of a cyclic carbonate with a small amount of impurities. Further, the production method can provide a novel cyclic carbonate to be described below.

The following cyclic carbonates among the cyclic carbonates to be obtainable by the production method of the invention are novel compounds.

The cyclic carbonate of the invention is represented by the following formula (1a):

[Chem. 24]

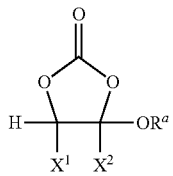

(1a)

wherein $X^1$ and $X^2$ are the same as or different from each other, and are each a hydrogen atom, a fluorine atom, or a monovalent organic group; and $R^a$ is a monovalent organic group containing one or more carbon-carbon triple bonds or a monovalent organic group containing a fluorine atom and one or more carbon-carbon unsaturated bonds.

Examples of $X^1$ and $X^2$ include those mentioned for the above production method of the invention, and the same applies to preferred embodiments.

For example, $X^1$ and $X^2$ are the same as or different from each other, and are each preferably a hydrogen atom, a fluorine atom, or an alkyl, aryl, alkoxyalkyl, or aryloxyalkyl group optionally containing a fluorine atom.

When $X^1$ is a substituent other than a hydrogen atom, the cyclic carbonate of the invention includes a stereoisomer. When including a stereoisomer, the cyclic carbonate of the invention may be a mixture containing a cis form and a trans form at any ratio or may be a compound represented by one of these structures.

$R^a$ is a monovalent organic group containing one or more carbon-carbon triple bonds or a monovalent organic group containing a fluorine atom and one or more carbon-carbon unsaturated bonds among the groups mentioned for R in the above formula (1).

The monovalent organic group containing a fluorine atom and one or more carbon-carbon unsaturated bonds is preferably a monovalent organic group containing a fluorine atom and a carbon-carbon double bond.

$R^a$ is preferably a C1-C10 alkyl group optionally containing one or both selected from a divalent or higher heteroatom and a fluorine atom. The C1-C10 alkyl group contains one or more carbon-carbon triple bonds or one or more carbon-carbon double bonds. When a carbon-carbon double bond is present, the substituents binding to the carbon-carbon double bond may form either an E-form geometrical isomer or a Z-form geometrical isomer, or may form a mixture thereof at any ratio.

Specific examples of the novel cyclic carbonate of the invention include the compounds mentioned as specific examples of the compound represented by the formula (1). Examples thereof include compounds in which R is a monovalent organic group containing one or more carbon-carbon triple bonds or a monovalent organic group containing a fluorine atom and one or more carbon-carbon unsaturated bonds.

In the cyclic carbonate of the invention, $X^1$ and $X^2$ are the same as or different from each other, and are each a hydrogen atom, a fluorine atom, or an alkyl, aryl, alkoxyalkyl, or aryloxyalkyl group optionally containing a fluorine atom, and $R^a$ is preferably a group represented by the following formula (C):

—($R^{b1}$)—C≡C-$L^1$ (C)

wherein $R^{b1}$ is an alkylene group optionally containing an oxygen atom or a carbon-carbon unsaturated bond between carbon atoms; and $L^1$ is a hydrogen atom, a fluorine atom, a C1-C7 silyl or aryl group optionally containing a fluorine atom, or a C1-C7 alkyl group optionally containing one or both selected from a divalent or higher heteroatom and a fluorine atom, a group represented by the following formula (D):

—($R^{b2}$)—$CL^2$=$CL^3L^4$ (D)

wherein $R^{b2}$ is a single bond or an alkylene group optionally containing an oxygen atom or an unsaturated bond between carbon atoms; $L^2$, $L^3$, and $L^4$ are the same as or different from each other, and are each a hydrogen atom, a fluorine atom, a C1-C8 silyl group optionally containing a fluorine atom, or a C1-C8 alkyl or aryl group optionally containing one or both selected from a divalent or higher heteroatom and a fluorine atom; and at least one selected from $L^2$, $L^3$, and $L^4$ contains a fluorine atom, or a group represented by the following formula (E'):

—($R^{b2}$)-$L^{5a}$ (E')

wherein $R^{b2}$ is defined as described above; $L^{5a}$ is a group containing an aromatic ring; and $L^{5a}$ contains a fluorine atom.

In the formula (D), the substituents binding to the carbon-carbon double bond may form either an E-form geometrical isomer or a Z-form geometrical isomer, or may form a mixture thereof at any ratio.

$R^{b1}$ preferably has a carbon number of 1 to 8, more preferably 1 to 5, still more preferably 1 to 3.

$R^{b2}$ preferably has a carbon number of 0 to 8, more preferably 0 to 5, still more preferably 1 to 3.

An example of $L^{5a}$ is a perfluorophenyl group.

A preferred example of the group represented by the formula (E') is an aryl group containing a fluorine atom.

The cyclic carbonate of the invention is also preferably a compound represented by the above formula (1-1).

$R^a$ is also preferably a C10 or lower alkyl group containing a divalent or higher heteroatom and one or more carbon-carbon unsaturated bonds, and the divalent or higher heteroatom is also preferably an oxygen atom or a silicon atom.

The cyclic carbonate of the invention has the above structure, and thus can be useful as any of a variety of chemicals such as pharmaceutical or agrochemical compounds and intermediates thereof.

The cyclic carbonate of the invention can be produced by the aforementioned production method of the invention.

EXAMPLES

The invention is described in more detail below with reference to examples. The physical properties were determined by the following methods.

Example 1

Production of 4-allyloxy-1,3-dioxolan-2-one

Vinylene carbonate (8.6 g, 100 mmol) and triethylamine (1.0 g, 10 mmol) were mixed. The system was purged with nitrogen, and allyl alcohol (5.8 g, 100 mmol) was dropwise added at 0° C. The components were stirred at room temperature for one hour. The reaction was followed by neutralization with 1 N hydrochloric acid, then washing with saturated baking soda water. The organic layer was dried and concentrated, whereby 13.1 g (yield: 91%) of the target product represented by the following formula was obtained.

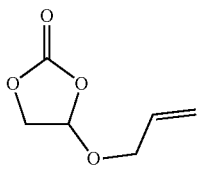

Example 2

Production of 4-(2-propynyloxy)-1,3-dioxolan-2-one

Vinylene carbonate (8.6 g, 100 mmol) and triethylamine (1.0 g, 10 mmol) were mixed. The system was purged with nitrogen, and propargyl alcohol (5.6 g, 100 mmol) was dropwise added at 0° C. The components were stirred at room temperature for one hour. The reaction was followed by neutralization with 1 N hydrochloric acid, then washing with saturated baking soda water. The organic layer was dried and concentrated, whereby 12.2 g (yield: 86%) of the target product represented by the following formula was obtained.

[Chem. 26]

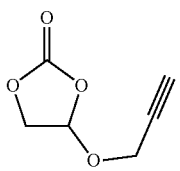

Example 3

Production of 4-{(3-trimethylsilyl)2-propynyloxy}-1,3-dioxolan-2-one

Vinylene carbonate (8.6 g, 100 mmol) and triethylamine (1.0 g, 10 mmol) were mixed. The system was purged with nitrogen, and 3-trimethylsilylpropargyl alcohol (12.8 g, 100 mmol) was dropwise added at 0° C. The components were stirred at room temperature for one hour. The reaction was followed by neutralization with 1 N hydrochloric acid, then washing with saturated baking soda water. The organic layer was dried and concentrated, whereby 18.2 g (yield: 85%) of the target product represented by the following formula was obtained.

[Chem. 27]

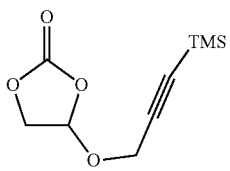

Example 4

Production of 4-allyloxy-4,5-dimethyl-1,3-dioxolan-2-one 4,5-Dimethyl vinylene carbonate (114 mg, 1 mmol) and triethylamine (10 mg, 0.1 mmol) were mixed. The system was purged with nitrogen, and allyl alcohol (58 mg, 1 mmol) was dropwise added at 0° C. The solution was returned to room temperature and stirred for one hour, whereby 137 mg (yield: 80%) of the target product represented by the following formula was obtained.

[Chem. 28]

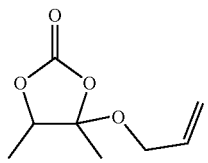

Example 5

Production of 4,5-dimethyl-4-(2-propynyloxy)-1,3-dioxolan-2-one 4,5-Dimethyl vinylene carbonate (114 mg, 1 mmol) and triethylamine (10 mg, 0.1 mmol) were mixed. The system was purged with nitrogen, and propargyl alcohol (56 mg, 1 mmol) was dropwise added at 0° C. The solution was returned to room temperature and stirred for one hour, whereby 144 mg (yield: 85%) of the target product represented by the following formula was obtained.

[Chem. 29]

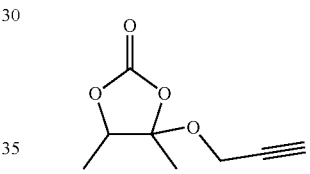

Example 6

Production of 4-(2-fluoroallyloxy)-1,3-dioxolan-2-one

Vinylene carbonate (86 mg, 1 mmol) and triethylamine (10 mg, 0.1 mmol) were mixed. The system was purged with nitrogen, and 2-fluoroallyl alcohol (76 mg, 1 mmol) was dropwise added at 0° C. The solution was returned to room temperature and stirred for one hour, whereby 146 mg (yield: 90%) of the target product represented by the following formula was obtained.

[Chem. 30]

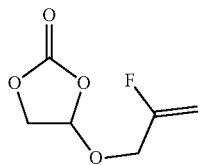

Example 7

Production of 4-(2-fluoroallyloxy)-4,5-dimethyl-1,3-dioxolan-2-one 4,5-Dimethyl vinylene carbonate (114 mg, 1 mmol) and triethylamine (10 mg, 0.1 mmol) were mixed. The system was purged with nitrogen, and 2-fluoroallyl alcohol (76 mg, 1 mmol) was dropwise added at 0° C. The solution was returned to room temperature and stirred for one hour, whereby 148 mg (yield: 78%) of the target product represented by the following formula was obtained.

[Chem. 31]

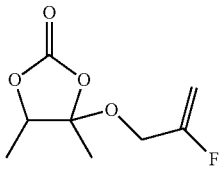

Example 8

Production of 4-((E)-4,4,4-trifluoro-2-butenoxy)-1,3-dioxolan-2-one

Vinylene carbonate (86 mg, 1 mmol) and triethylamine (10 mg, 0.1 mmol) were mixed. The system was purged with nitrogen, and (E)-4,4,4-trifluoro-2-buten-1-ol (126 mg, 1 mmol) was dropwise added at 0° C. The solution was returned to room temperature and stirred for one hour, whereby 195 mg (yield: 92%) of the target product represented by the following formula was obtained.

[Chem. 32]

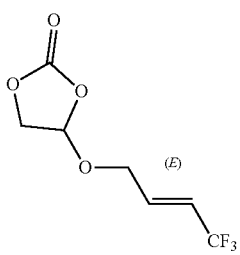

Example 9

Production of 4-((Z)-4,4,4-trifluoro-2-butenoxy)-1,3-dioxolan-2-one

Vinylene carbonate (86 mg, 1 mmol) and triethylamine (10 mg, 0.1 mmol) were mixed. The system was purged with nitrogen, and (Z)-4,4,4-trifluoro-2-buten-1-ol (126 mg, 1 mmol) was dropwise added at 0° C. The solution was returned to room temperature and stirred for one hour, whereby 190 mg (yield: 90%) of the target product represented by the following formula was obtained.

[Chem. 33]

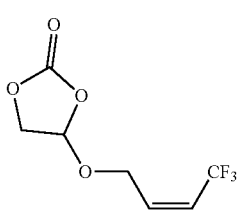

Example 10

Production of 4-((E,Z)-4,4,4-trifluoro-2-butenoxy)-1,3-dioxolan-2-one

Vinylene carbonate (86 mg, 1 mmol) and triethylamine (10 mg, 0.1 mmol) were mixed. The system was purged with nitrogen, and (E,Z)-4,4,4-trifluoro-2-buten-1-ol (126 mg, 1 mmol, E form:Z form=50:50) was dropwise added at 0° C. The solution was returned to room temperature and stirred for one hour, whereby 190 mg (yield: 90%) of the target product represented by the following formula was obtained.

[Chem. 34]

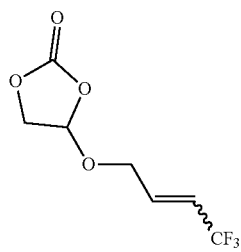

Example 11

Production of 4-((E)-4,4,4-trifluoro-2-butenoxy)-4,5-dimethyl-1,3-dioxolan-2-one 4,5-Dimethyl vinylene carbonate (86 mg, 1 mmol) and triethylamine (10 mg, 0.1 mmol) were mixed. The system was purged with nitrogen, and (E)-4,4,4-trifluoro-2-buten-1-ol (126 mg, 1 mmol) was dropwise added at 0° C. The solution was returned to room temperature and stirred for one hour, whereby 163 mg (yield: 68%) of the target product represented by the following formula was obtained.

[Chem. 35]

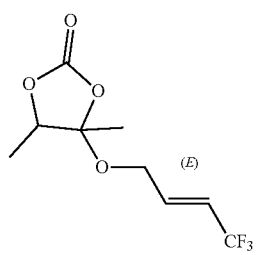

Example 12

Production of 4-((Z)-4,4,4-trifluoro-2-butenoxy)-4,5-dimethyl-1,3-dioxolan-2-one 4,5-Dimethyl vinylene carbonate (86 mg, 1 mmol) and triethylamine (10 mg, 0.1 mmol) were mixed. The system was purged with nitrogen, and (Z)-4,4,4-trifluoro-2-buten-1-ol (126 mg, 1 mmol) was dropwise added at 0° C. The solution was returned to room temperature and stirred for one hour, whereby 158 mg (yield: 66%) of the target product represented by the following formula was obtained.

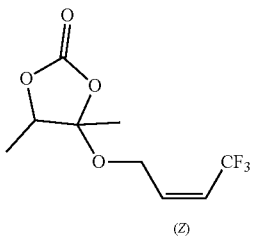

(Z)

Example 13

Production of 4-((E,Z)-4,4,4-trifluoro-2-butenoxy)-4,5-dimethyl-1,3-dioxolan-2-one 4,5-Dimethyl vinylene carbonate (86 mg, 1 mmol) and triethylamine (10 mg, 0.1 mmol) were mixed. The system was purged with nitrogen, and (E,Z)-4,4,4-trifluoro-2-buten-1-ol (126 mg, 1 mmol, E form:Z form=50:50) was dropwise added at 0° C. The solution was returned to room temperature and stirred for one hour, whereby 158 mg (yield: 66%) of the target product represented by the following formula was obtained.

[Chem. 37]

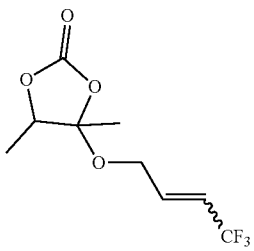

Example 14

Production of 4-phenoxy-1,3-dioxolan-2-one

Vinylene carbonate (86 mg, 1 mmol) and triethylamine (10 mg, 0.1 mmol) were mixed. The system was purged with nitrogen, and phenol (109 mg, 1 mmol) was dropwise added at 0° C. The solution was returned to room temperature and stirred for one hour, whereby 126 mg (yield: 70%) of the target product represented by the following formula was obtained.

[Chem. 38]

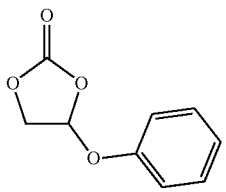

INDUSTRIAL APPLICABILITY

The production method of the invention can provide a novel cyclic carbonate. The novel cyclic carbonate of the invention can be used as any of a variety of chemicals such as pharmaceutical or agrochemical compounds and intermediates thereof.

The invention claimed is:

1. A method for producing a cyclic carbonate represented by the following formula (1a):

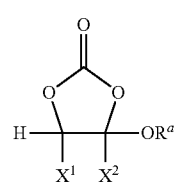

(1a)

wherein $X^1$ and $X^2$ are the same as or different from each other, and are each a hydrogen atom, a fluorine atom, or a monovalent organic group; $R^a$ has a carbon number of 1 to 10, and $R^a$ is a group represented by the following formula (C):

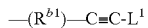

$$-(R^{b1})-C\equiv C-L^1 \quad (C)$$

wherein $R^{b1}$ is an alkylene group optionally containing an oxygen atom or a carbon-carbon unsaturated bond between carbon atoms; and $L^1$ is a hydrogen atom, a fluorine atom, a C1-C7 silyl or aryl group optionally containing a fluorine atom, or a C1-C7 alkyl group optionally containing one or both selected from a divalent or higher heteroatom and a fluorine atom;

a group represented by the following formula (D):

$$-(R^{b2})-CL^2=CL^3L^4 \quad (D)$$

wherein $R^{b2}$ is an alkylene group optionally containing an oxygen atom or an unsaturated bond between carbon atoms; $L^2$, $L^3$, and $L^4$ are the same as or different from each other, and are each a hydrogen atom, a fluorine atom, a C1-C8 silyl group optionally containing a fluorine atom, or a C1-C8 alkyl or aryl group optionally containing one or both selected from a divalent or higher heteroatom and a fluorine atom; at least one selected from $L^2$, $L^3$, and $L^4$ contains a fluorine atom, or a group represented by the following formula (E'):

$$(R^{b2})-L^{5a} \quad (E')$$

wherein $R^{b2}$ is defined as described above; $L^{5a}$ is a group containing an aromatic ring, and $L^{5a}$ contains a fluorine atom, the method comprising reacting an unsaturated cyclic carbonate represented by the following formula (A):

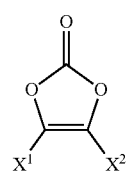

(A)

wherein $X^1$ and $X^2$ are defined as described above, and an alcohol represented by the following formula (B):

$$R^a-OH \quad (B)$$

wherein $R^a$ is defined as described above, or an alkoxide thereof in the presence of a base, or reacting the unsaturated cyclic carbonate and the alkoxide.

2. The method for producing a cyclic carbonate according to claim 1, wherein $X^1$ and $X^2$ are the same as or different from each other, and are each a hydrogen atom, a fluorine atom, or an alkyl, aryl, alkoxyalkyl, or aryloxyalkyl group optionally containing a fluorine atom.

3. The method for producing a cyclic carbonate according to claim 1, wherein $R^a$ is a C1-C10 organic group containing one or more carbon-carbon unsaturated bonds and optionally containing one or both selected from a divalent or higher heteroatom and a fluorine atom.

4. The method for producing a cyclic carbonate according to claim 1, wherein $R^a$ is a C1-C10 organic group containing a divalent or higher heteroatom and one or more carbon-carbon unsaturated bonds.

5. The method for producing a cyclic carbonate according to claim 4, wherein the divalent or higher heteroatom is an oxygen atom or a silicon atom.

6. The method for producing a cyclic carbonate according to claim 1, wherein the base includes at least one selected from the group consisting of a hydride of an alkali metal or an alkaline earth metal, a hydroxide of an alkali metal or an alkaline earth metal, a carbonate compound of an alkali metal or an alkaline earth metal, a hydrogencarbonate compound of an alkali metal, an alkoxide of an alkali metal or an alkaline earth metal, an amide of an alkali metal or an alkaline earth metal, guanidine, and an amine.

7. A cyclic carbonate represented by the following formula (1a):

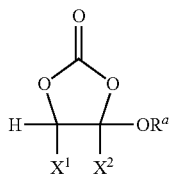

(1a)

wherein $X^1$ and $X^2$ are the same as or different from each other, and are each a hydrogen atom, a fluorine atom, or a monovalent organic group;

$R^a$ has a carbon number of 1 to 10, and $R^a$ is a group represented by the following formula (C):

$$—(R^{b1})—C≡C-L^1 \qquad (C)$$

wherein $R^{b1}$ is an alkylene group optionally containing an oxygen atom or a carbon-carbon unsaturated bond between carbon atoms; and $L^1$ is a hydrogen atom, a fluorine atom, a C1-C7 silyl or aryl group optionally containing a fluorine atom, or a C1-C7 alkyl group optionally containing one or both selected from a divalent or higher heteroatom and a fluorine atom;

a group represented by the following formula (D):

$$—(R^{b2})—CL^2=CL^3L^4 \qquad (D)$$

wherein $R^{b2}$ is an alkylene group optionally containing an oxygen atom or an unsaturated bond between carbon atoms; $L^2$, $L^3$, and $L^4$ are the same as or different from each other, and are each a hydrogen atom, a fluorine atom, a C1-C8 silyl group optionally containing a fluorine atom, or a C1-C8 alkyl or aryl group optionally containing one or both selected from a divalent or higher heteroatom and a fluorine atom; at least one selected from $L^2$, $L^3$, and $L^4$ contains a fluorine atom, or a group represented by the following formula (E'):

$$—(R^{b2})-L^{5a} \qquad (E')$$

wherein $R^{b2}$ is defined as described above; $L^{5a}$ is a group containing an aromatic ring, and $L^{5a}$ contains a fluorine atom.

8. The cyclic carbonate according to claim 7, wherein $X^1$ and $X^2$ are the same as or different from each other, and are each a hydrogen atom, a fluorine atom, or an alkyl, aryl, alkoxyalkyl, or aryloxyalkyl group optionally containing a fluorine atom.

9. The cyclic carbonate according to claim 7, wherein $R^a$ is a C1-C10 organic group optionally containing one or both selected from a divalent or higher heteroatom and a fluorine atom.

10. The cyclic carbonate according to claim 7, wherein $R^a$ is a C10 or lower organic group containing a divalent or higher heteroatom and one or more carbon-carbon unsaturated bonds.

11. The cyclic carbonate according to claim 10, wherein the divalent or higher heteroatom is an oxygen atom or a silicon atom.

* * * * *